United States Patent [19]
Cipolli et al.

[11] Patent Number: 5,104,986
[45] Date of Patent: Apr. 14, 1992

[54] TRIAZINIC COMPOUNDS

[75] Inventors: Roberto Cipolli, Seregno; Enrico Masarati, Castelnovo Valtidone; Gilberto Nucida, S. Giuliano Milanese; Roberto Oriani, Bergamo, all of Italy

[73] Assignee: Ministero Dell' Universita' e Della Ricerca Scientifica e Tecnologia, Rome, Italy

[21] Appl. No.: 572,453

[22] Filed: Aug. 27, 1990

[30] Foreign Application Priority Data

Mar. 27, 1990 [IT] Italy ................. 19840 A/90

[51] Int. Cl.$^5$ ............... C07D 403/12; C07D 403.14; C07D 401/12; C07D 401/14
[52] U.S. Cl. ...................... 544/198; 544/60; 544/113; 544/83
[58] Field of Search ............... 544/198, 60, 113, 83

[56] References Cited

U.S. PATENT DOCUMENTS

| | | | |
|---|---|---|---|
| 4,348,493 | 9/1982 | Loffelman | 544/198 |
| 4,547,548 | 10/1985 | Cantatore | 544/198 |
| 4,629,752 | 12/1986 | Layer et al. | 544/198 |
| 4,639,479 | 1/1987 | Lai et al. | 544/198 |
| 4,691,015 | 9/1987 | Behrens et al. | 544/198 |

Primary Examiner—John M. Ford
Attorney, Agent, or Firm—Stevens, Davis, Miller & Mosher

[57] ABSTRACT

Triazinic compounds of general formula (I):

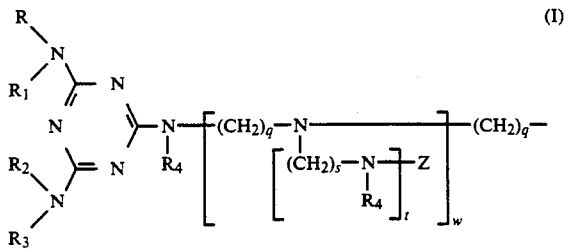

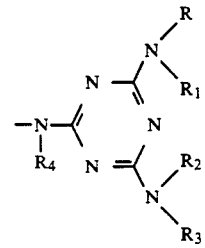

obtained by the reaction of one mole of a halide of cyanuric acid with two moles of an amine, and following reaction of the so obtained intermediate with a polyamine.

The compounds of general formula (I) find a use, in particular, as flame-retardant additives for polymers.

3 Claims, No Drawings

TRIAZINIC COMPOUNDS

BACKGROUND OF THE INVENTION

The present invention relates to triazinic compounds.

More particularly, the present invention relates to novel compounds derivatives of 2,4,6-triamino-1,3,5-triazine, which are capable of endowing the thermoplastic polymers, or the polymers with elastomeric properties, in particular olefinic polymers of copolymers, with high self-extinguishing characteristics, when said polymers are exposed to a flame.

In particular, the subject matter of the present invention are triazinic compounds having the general formula (I):

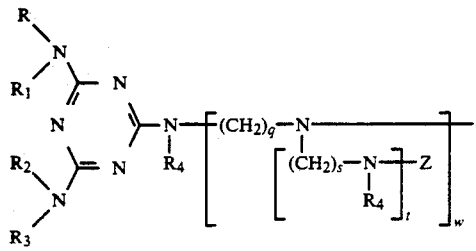

t is either 0 or 1;
when t is equal to 0:
at least one of the radicals from R to R$_3$ is:

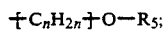

$-\!\!+\!C_nH_{2n}\!\!+\!O\!-\!R_5$;

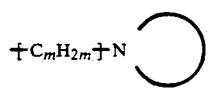

wherein:
n = an integer within the range of from 2 to 8;
m = an integer within the range of from 2 to 6;
R$_5$ = H; (C$_1$-C$_8$)-alkyl; (C$_2$-C$_6$)-alkenyl; $-\!\!+\!C_pH_{2p}\!\!+\!$O-R$_6$, wherein p is an integer comprised within the range of from 1 to 4 and R$_6$ is either H or a (C$_1$-C$_4$)-alkyl; (C$_6$-C$_{12}$)-cycloalkyl or (C$_6$-C$_{12}$)-alkylcycloalkyl;
the group:

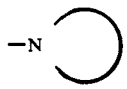

is replaced by a heterocyclic radical bonded to the alkyl chain through the nitrogen atom, and optionally containing another heteroatom preferably selected from among O, S, N; or in general formula (I) at least one of the moieties:

is replaced by a heterocyclic radical linked to the triazinic ring through the nitrogen atom and optionally containing another heteroatom preferably selected from the group consisting of O, S N; the other radicals from R to R:, which are either equal to, or different from one another, and can have different meanings in each triazinic ring, have the abovesaid meaning, or they are: H; (C$_1$-C$_{18}$)-alkyl; (C$_2$-C$_8$)-alkenyl; (C$_6$-C$_{16}$)-cycloalkyl or (C$_6$-C$_{16}$)-alkylcycloalkyl, optionally substituted with a hydroxy or (C$_1$-C$_{C4}$)-hydroxyalkyl function;

when t is equal to 1 the radicals from R to R$_3$, which are either equal to, or different from one another, and can have different meanings in each triazinic ring are: H; (C$_1$-C$_{18}$)-alkyl; (C$_2$-C$_8$)-alkenyl; (C$_6$-C$_{16}$)-cycloalkyl or (C$_6$-C$_{16}$)-alkylcycloalkyl, optionally substituted with a hydroxy or (C$_1$-C$_4$)-hydroxyalkyl function;

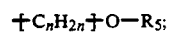

$-\!\!+\!C_nH_{2n}\!\!+\!O\!-\!R_5$;

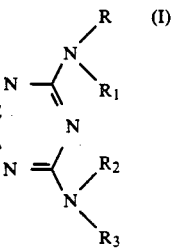

wherein:
n = an integer within the range of from 2 to 8;
m = an integer within the range of from 2 to 6;
R$_5$ = H; (C$_1$-C$_8$)-alkyl; (C$_2$-C$_6$)-alkenyl; $-\!\!+\!C_pH_{2p}\!\!+\!$O-R$_6$, wherein p is an integer comprised within the range of from 1 to 4 and R$_6$ is either H or a (C$_1$-C$_4$)-alkyl; (C$_6$-C$_{12}$)-cycloalkyl or (C$_6$-C$_{12}$)-alkylcycloalkyl;
the radicals R$_7$, which can be either equal to, or different from one another, are: H; (C$_1$-C$_8$)-alkyl; (C$_2$-C$_6$)-alkenyl; (C$_6$-C$_{12}$)-cycloalkyl or (C$_6$-C$_{12}$)-alkylcycloalkyl; (C$_1$-C$_4$)-hydroxyalkyl; or the moiety:

is replaced by a heterocyclic radical linked to the alkyl chain through the nitrogen atom and optionally containing another heteroatom preferably selected from the group consisting of O, S, N; or in general formula (I) at least one of the moieties:

is replaced by a heterocyclic radical linked to the triazinic ring through the nitrogen atom and optionally containing another heteroatom preferably selected from the group consisting of O, S, N; R$_4$ is either hydrogen or (C$_{-C4}$)-alkyl; the indexes g, which can be either equal to, or different from, each other, are integers comprised within the range of from 2 to 5; s is an integer within the range of from 2 to 4; w is an integer within the range of from 1 to 5; Z is a hydrogen atom or:

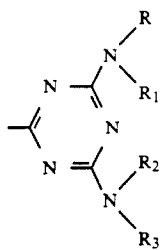

and its meaning can vary inside each repeating unit. Belonging to compounds of general formula (I) are also those derivatives having asymmetrical structure in that the radical from R to $R_3$ can have different meanings in each triazinic ring.

Examples of radicals from R to $R_3$ in the above general formula (I) are: methyl; ethyl; propyl; isopropyl; n-butyl; isobutyl; tert-butyl; n-pentyl; isopentyl; n-hexyl; tert-hexyl; octyl; tert-octyl; decyl; dodecyl; octadecyl; ethenyl; propenyl; butenyl; isobutenyl; hexenyl; octenyl; cyclohexyl; propylcyclohexyl; butyl cyclohexyl; decyl cyclohexyl; idroxycyclohexyl; idroxyethyl cyclohexyl; 2-hydroxyethyl; 2-hydroxypropyl; 3-hydroxypropyl; 3-hydroxybutyl; 4-hydroxybutyl; 3-hydroxypentyl; 5-hydroxypentyl; 6-hydroxyhexyl; 3-hydroxy-2,5-dimethyl hexyl; 7-hydroxyheptyl; 7-hydroxyoctyl; 2-methoxy ethyl; 2-methoxy propyl; 3-methoxy propyl; 4-methoxy butyl; 6-methoxy hexyl; 7-methoxyheptyl; 7-methoxy octyl; 2-ethoxy ethyl; 3-ethoxy propyl; 4-ethoxy butyl; 3-propoxy propyl; 3-butoxy propyl; 4-butoxy-butyl; 4-isobutoxy butyl; 5-propoxy pentyl; 2-cyclohexyloxyethyl; 2-ethenyloxy ethyl; 2-(N,N-dimethylamino)ethyl; 3-(N,N-dimethylamino)propyl; 4-(N,N-dimethylamino)butyl; 5-N,N-dimethylamino)pentyl; 4-(N,N-diethylamino)butyl; 5-(N,N-diethylamino)pentyl; 5-(N,N-di-isopropylamino)pentyl; 3-(N-ethylamino)propyl; 4-(N-methylamino)butyl; 4-(N,N-dipropylamino)butyl; 2-(N,N-diisopropylamino)ethyl; 6-(N-hexenylamino)-hexyl; 2-(N-ethenylamino)ethyl; 2-(N-cyclohexylamino)ethyl; 2-(N-2-hydroxyethylamino)ethyl; 2-(2-hydroxyethoxy)ethyl; 2-(2-methoxyethoxy)ethyl; and so forth.

Examples of heterocyclic radicals which can replace the moieties:

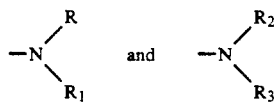

are: aziridine; pyrrolidine; piperidine; morpholine; thiomorpholine; piperazine; 4-methyl piperazine; 4-ethylpiperazine; 2-methyl piperazine; 2,5-dimethyl piperazine; 2,3,5,6-tetramethyl piperazine; 2-ethyl piperazine; 2,5-diethyl piperazine; and so forth.

Triazinic compounds according to the present invention are also those on which the moieties:

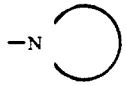

-continued and

are substituted by a heterocyclic radical selected from among the following: aziridine; pyrrolidine; piperidine; morpholine; thiomorpholine; piperazine; 4-methyl piperazine; 4-ethylpiperazine; and so forth.

Examples of polyvalent radicals

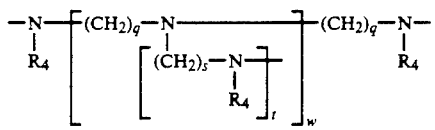

are those which derive, by elimination of a hydrogen atom from each reacted amino group, from the following polyaminic compounds: bis(2-aminoethyl)amine; bis(3-aminopropyl)amine; bis(4-aminobutyl)amine; bis(5-aminopentyl)amine; bis[2-(N-methylamino)ethyl]amine; 2-N-butyl bis(2-aminoethyl)amine; bis[3-(N-methylamino)propyl]-amine; N-(3-aminopropyl)-1,5-diamino pentane; N-(4-aminobutyl)-1,5-diamino pentane; tris(2-aminoethyl)amine; tris(3-aminopropyl)amine; tris(4-aminobutyl)amine; tris[2-(N-ethylamino)ethyl]amine; N,N'-bis(2-aminoethyl)-1,2-diamino ethane; N,N'-bis(3-aminopropyl)-1,3-diaminopropane; N,N'-bis(2-aminoethyl)-1,3-diamino propane; N,N'-bis(3-aminopropyl)-1,2-diamino ethane; N,N'-bis(3-aminopropyl-1,4-diaminobutane; bis[2-(2-aminoethyl)-aminoethyl]amine; N,N' bis-[2-(2-aminoethyl)aminoethyl]-1,2-diamino ethane; N,N,-bis[3-(2-aminoethyl) aminopropyl]-1,2-diamino ethane; N,N,N',N'-tetrakis(2-aminoethyl)-1,2-diamino ethane; and so forth.

Specific compounds comprised within the scope of general formula (I) are reported in the examples which follow the instant disclosure.

The compounds of general formula (I) can be prepared by reacting, at temperatures comprised within the range of from 0° to 10° C., and at a pH value comprised within the range of from 5 to 7, a halide of cyanuric acid, such as, e.g., cyanuric chloride, in a suitable solvent (such as, e.g., acetone, water, methylene chloride, and so forth) with an amine having the general formula (II):

wherein R and $R_1$ have the hereinabove defined meaning, in the presence or less (according to the molar ratio used in the reaction) of an acid acceptor (such as, e.g., NaOH, NaHCO$_3$, Na$_2$CO$_3$, triethylamine, and so forth) with the intermediate (III):

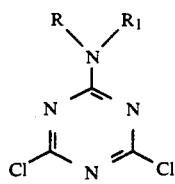
(III)

being obtained.

Such an intermediate, either separated or not separated from the reaction mixture, is subsequently reacted under conditions similar to those as hereinabove specified, but operating at a temperature comprised within the range of from 10° to 50° C. and an amine of general formula (IV):

wherein $R_2$ and $R_3$ have the hereinabove defined meaning, with the intermediate (V):

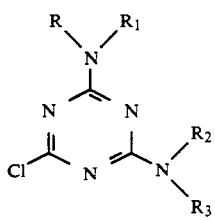
(V)

being obtained.

The intermediate (V), either separated or not and in a number of moles smaller than, or equal to, $(2+w)$, is reacted in its turn, under the same conditions as of the two first reaction steps, but operating at higher temperature than of the preceding step, e.g., comprised within the range of from 70° to 150° C. and hence with a solvent being used which is compatible with such temperature values (such as, e.g., water, toluene, xylene, dimethylformamide, and so forth), with one mole of a polyamine having the general formula (VI):

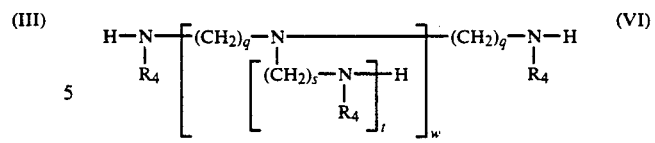
(VI)

wherein $R_4$, q, s, t, and w have the same meaning as defined hereinabove, with the compounds of general formula (I) being obtained as the end products.

In case compounds of general formula (I) containing equal moieties

are desired, the process is carried out by reacting cyanuric chloride with two moles of an amine of general formula (II) under the same conditions as disclosed hereinabove in order to obtain the intermediate of general formula (V).

An alternative method consists of reacting a number of moles lower than, or equal to, $(2+w)$ of a halide, such as, e.g., the chloride, of cyanuric acid with one mole of a polyamine of general formula (VI) as above defined, still under the same conditions as hereinabove disclosed, at a temperature comprised within the range of from 0° to 10° C. in order to yield the intermediate of general formula (VII):

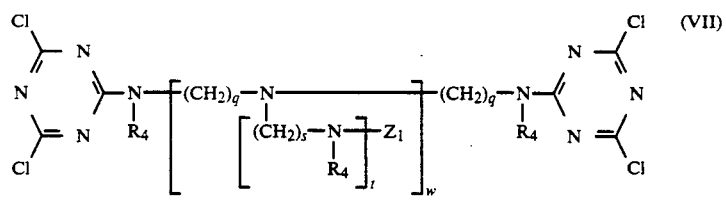
(VII)

wherein Z is hydrogen or:

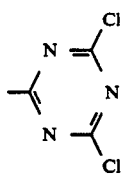

and its meaning can vary inside each repeating unit.

Such an intermediate, either separated or not, is reacted once again:

(a) with a number of moles lower than, or equal to $(2+w)$ or an amine of general formula (II), at a temperature comprised within the range of from 40° to 80° C. in order to yield the intermediate of general formula (VIII):

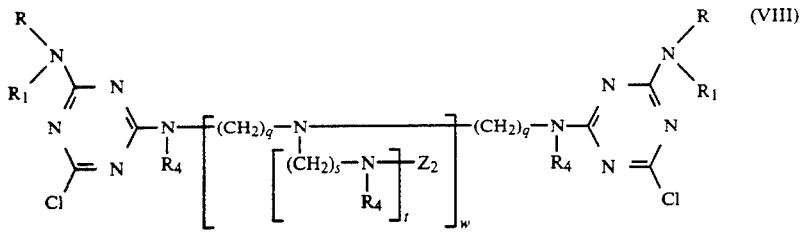

wherein $Z_2$ is hydrogen or

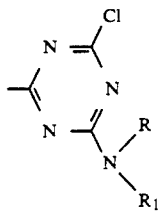

and its meaning can vary inside each repeating unit; which intermediate, once again either separated or not, is reacted with a number of moles lower than, or equal to (2+w) of an amine of general formula (IV), at a temperature comprised within the range of from 80° to 150° C. and under similar conditions as those disclosed hereinabove; or (b) with a number of moles lower than, or equal to 2(2+w) of an amine of general formula (II), at a temperature comprised within the range of from 80° to 150° C., under similar conditions as disclosed hereinabove.

Good quality products of general formula (I) are generally obtained as a white crystalline powder, which can be used in the self-extinguishing polymeric compositions without further purifications.

EXAMPLES

The following Examples are reported in order to illustrate the characteristics of the invention without limiting them.

EXAMPLE 1

184.5 g of cyanuric chloride and 1300 cm³ of methylene chloride are charged to a reactor of 3 liters of capacity, equipped with stirrer, thermometer, charging funnel, reflux condenser and cooling bath.

With the reaction mixture being cooled from the outside, 87.2 g of morpholine and 40 g of sodium hydroxide dissolved in 150 g of water are simultaneously added to the reaction mixture, within a 3 hours time, with the pH value of said reaction mixture being kept comprised within the range of from 5 to 7, and the temperature being comprised within the range of from 0° to 3° C.

The reaction mass is kept at the temperature of from 0° to 3° C. for a further 3 hours, and the aqueous phase is then separated.

By distillation of methylene chloride, 230 g of intermediate (IX):

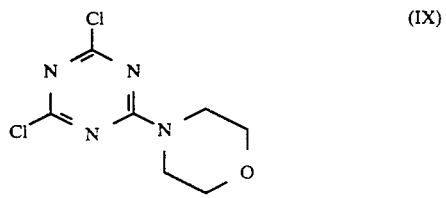

is obtained as a white crystalline powder having a melting point (m.p.) of 155°–157° C. and a chlorine content of 29.87% (theoretical value: 30.21%).

To a reactor of 1 liter of capacity, equipped as the preceding one, but provided with a heating bath, 200 g of an aqueous solution at 30% by weight of ammonia, 200 cm³ of water and 141 g of intermediate (IX) are charged.

The reaction mixture is heated to 50° C., and is kept at this temperature for 7 hours. It is then cooled down to room temperature, the precipitated solid product is filtered off and is washed with water.

By drying the filtration cake, 116 g of intermediate (X):

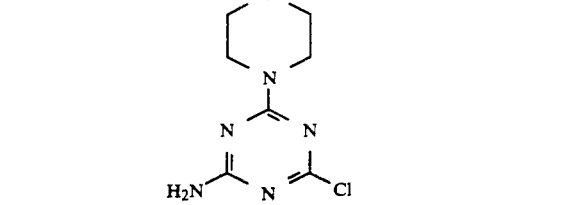

is obtained as a white crystalline powder having m.p.=189°–191° C. and a chloride content of 16.28% (theoretical value: 16.47%).

The structure of compounds (IX) and (X) was confirmed by I.R. spectroscopic analysis.

400 cm³ of xylene, 64.7 g of intermediate (X) and 10.3 g of diethylene triamine are charged to a reactor of 1 liter of capacity, equipped as the hereinabove disclosed one.

The reaction mixture is heated to 100° C. and is kept at this temperature for 2 hours. Then 12 g of sodium hydroxide is added and the reaction mixture is heated to boiling temperature.

The reaction mass is refluxed for 24 hours, then is cooled down to room temperature and the precipitated solid product is filtered off, with the filter cake being washed with plentiful water.

By oven-drying at 100° C., 56.7 g of product:

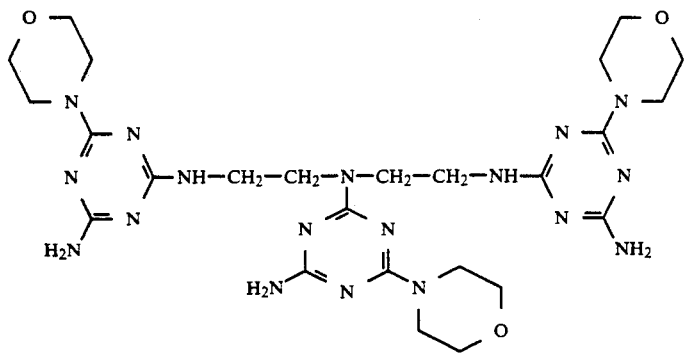

is obtained as a crystalline powder having m.p.=207°-208° C.

EXAMPLE 2

184.5 g of cyanuric chloride and 800 cm³ of acetone are charged to a reactor of 3 liters of capacity, equipped with stirrer, thermometer, charging funnel, reflux condenser and heating bath.

The reaction mixture is stirred and is simultaneously heated up to 40° C., until a solution is obtained; then, with the temperature being kept constant at the value of 40° C., 284 g of an ammonia solution at 30% by weight is added within a 1 hour and 30 minutes time.

The reaction mixture is subsequently heated to 45° C., and is maintained 4 hours at this temperature.

After cooling, the precipitated solid is filtered off and the filter cake is washed with water on the same filter.

After oven-drying at 100° C., 113 g of intermediate (XI):

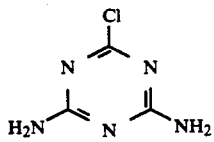

(XI)

is obtained as a white, infusible, crystalline powder having a chlorine content of 24.2% (theoretical value: 24.4%).

The structure of this compound was also confirmed by I.R. spectroscopic analysis.

500 cm³ of water, 87.3 g of intermediate (XI) and 29.2 g of tris (2-aminoethyl) amine are charged to a reactor of 1 liter of capacity, equipped as the hereinabove disclosed one.

The reaction mixture is heated to 50° C. and is kept at this temperature for 1 hour.

Then 24.0 g of sodium hydroxide dissolved in 50 cm³ of water is added over a 3 hours time, and the reaction mixture is simultaneously heated to boiling temperature.

The reaction mass is refluxed for about 10 hours, then is cooled down to room temperature and the precipitated solid product is filtered off.

The filter cake is washed with water and is dried. 89.4 g of product:

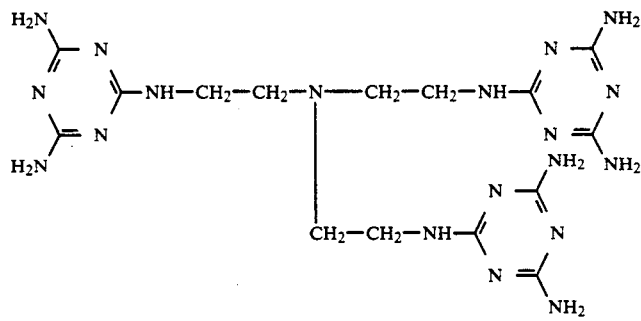

is obtained as a white crystalline powder having m.p.=125°-130° C.

EXAMPLE 3

184.5 g of cyanuric chloride and 1300 cm³ of methylene chloride are charged to a reactor of 3 liters of capacity, equipped in the same way as of Example 1.

With the reaction mixture being cooled by means of an external cooling, 75 g of 2-methoxyethylamine and 40 g of sodium hydroxide dissolved in 150 cm³ of water are simultaneously added to the reaction mixture, within a 3 hours time, with the pH value of said reaction mixture being kept comprised within the range of from 5 to 7, and the temperature thereof being kept comprised within the range of from 0° to 3° C.

The reaction mixture is kept at a temperature comprised within the range of from 0° to 3° C. for a further 3 hours, and the aqueous phase is then separated.

The organic solution is treated with two portions, of 200 cm³ each, of water, with the aqueous phase being separated each time.

By distilling off methylene chloride, 217.5 g of intermediate (XII):

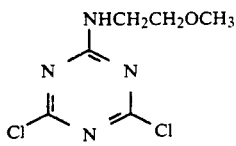
(XII)

is obtained as a white crystalline powder having m.p.=73°-75° C. and a chlorine content of 31.68% (theoretical value: 31.84%).

To a reactor of 1 liter of capacity, equipped with a stirrer, a thermometer, a charging funnel, a reflux condenser and a heating bath, 400 cm$^3$ of acetone and 133.8 g of intermediate (XII) are charged.

The reaction mixture is heated with stirring up to 40° C. until a solution is obtained, then, with the temperature of the reaction mixture being still kept at 40° C., 102 g of an aqueous solution of ammonia at 30% by weight is added within a 30 minutes time.

The reaction mixture is subsequently heated to 45° C. and is maintained 4 hours at this temperature.

After cooling down to 10° C., the precipitated solid product is filtered off, and the filtration cake is washed on the same filter with cold water.

After oven-drying at 100° C., 114 g of the intermediate product (XIII):

(XIII)

is obtained as a crystalline powder having m.p.=195°-197° C. and a chlorine content of 17.18% (theoretical value: 17.44%).

The structure of the intermediates (XII) and (XIII) was confirmed by I.R.-spectroscopic analysis.

500 cm$^3$ of ortho-dichlorobenzene, 91.6 g of intermediate (XIII) and 21.9 g of tris(2-aminoethyl)amine are charged to a reactor of 1 liter of capacity, equipped in the same way as of the preceding reactor.

The reaction mixture is heated to 100° C. and is maintained at that temperature for 2 hours. Then 18 g of sodium hydroxide is added and the temperature is increased up to 140° C. The reaction mass is maintained at 140° C for 16 hours, then is cooled to room temperature and the precipitated solid product is filtered off. The filtration cake is washed with plentiful water.

After drying the filtration cake, 88.2 g of product:

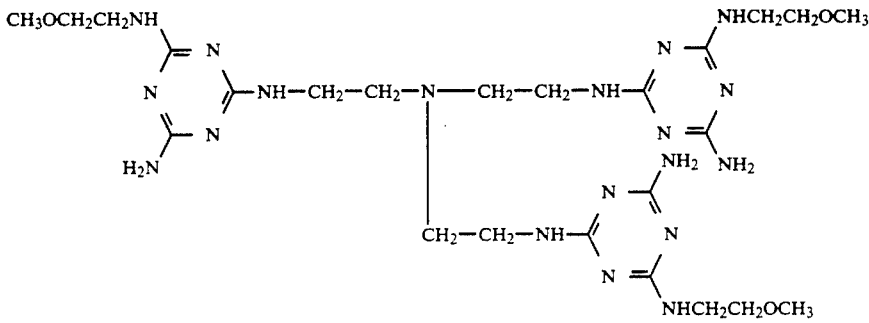

is obtained as a crystalline powder having m.p.=190°-195° C.

EXAMPLE 4

500 cm$^3$ of xylene, 86.2 g of intermediate (X) and 15.1 g of tetraethylenepentamine are charged to the same reaction equipment of 1 liter of capacity as of Example 3.

The reaction mass is heated up to 80° C. and is maintained at that temperature for 2 hours. 16 g of sodium hydroxide is then added and the temperature is increased up to 110° C.

The reaction mass is maintained at 110° C. for 18 hours, then is cooled down to room temperature and the precipitated solid product is filtered off and the filtration cake is washed with plentiful water.

After oven-drying the cake at 100° C., 82.6 g of product:

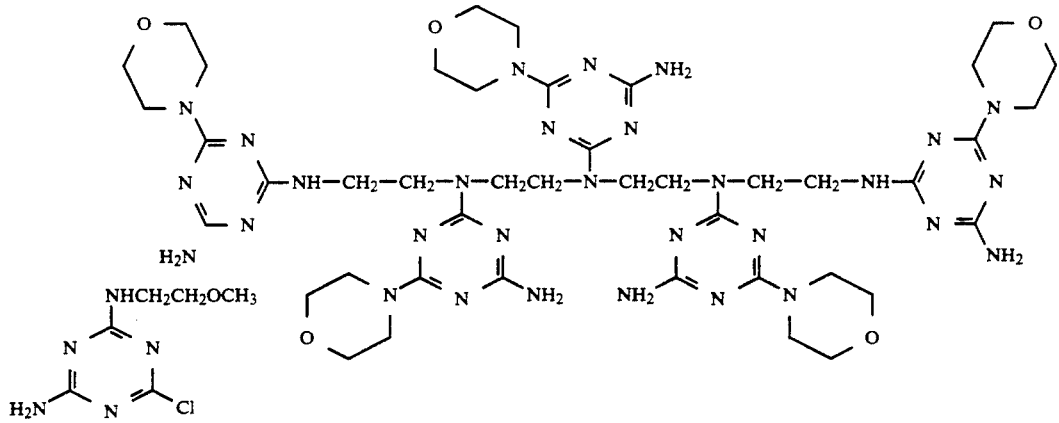

is obtained as a crystalline powder with m.p.=178°-183° C.

EXAMPLE 5

55.3 g of cyanuric chloride and 300 cm³ of acetone are charged to a reactor of 1 liter of capacity equipped in the same was as of Example 1.

With the reaction mixture being kept cooled at a temperature of 0°–5° C. by means of an external cooling, 10.3 g of diethylenetriamine dissolved in 200 cm³ of acetone is added within a 1 hour time.

With the reaction temperature being still kept comprised within the range of from 0° to 5° C., 12 g of sodium hydroxide dissolved in 100 g of water is added.

The reaction mixture is stirred at 5° C. for a further 4 hours time, then 200 g of cold water is added, the precipitated solid product is filtered off and the filtration cake is washed with water on the same filter.

After drying, 45.6 g of the intermediate (XIV):

(XIV)

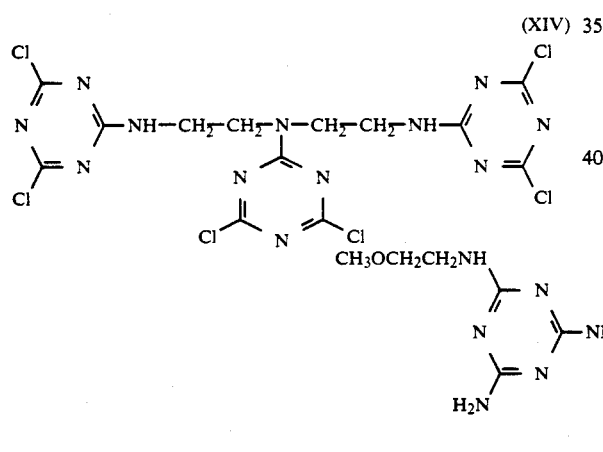

is obtained as a crystalline white powder with a m.p. higher than 300° C. and a chlorine content of 38.46% (theoretical value: 38.94%).

To the same reactor of 1 liter of capacity, this time equipped with a heating bath, 500 cm³ of xylene and 32.8 g of intermediate (XIV) are charged.

The reaction mixture is heated to the temperature of 80° C. and subsequently 31.3 g of morpholine and then 14.4 g of sodium hydroxide in 50 g of water are added within a 4-hours time.

The temperature is gradually increased with water being removed by azeotropic distillation, until the solvent boiling temperature is reached.

The reaction mixture is kept 8 hours under refluxing conditions, then is cooled down to room temperature and is filtered. The filtration cake is thoroughly washed with water.

After drying, 43.1 g of product:

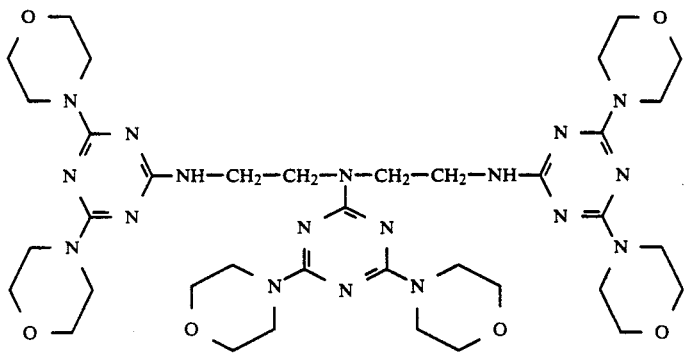

is obtained as a white crystalline powder having m.p.=277°–280° C.

EXAMPLE 6

450 cm³ of water, 91.6 g of intermediate (XIII) and, with stirring, 15.4 g of diethylenetriamine are charged to the same reactor of 1 liter of capacity as of Example 2.

The reaction mass is heated up to 80° C. and is maintained at that temperature for 3 hours.

18 g of sodium hydroxide dissolved in 30 cm³ of water is then added and the temperature of the reaction mixture is increased up to its boiling point. The reaction mass is refluxed for 16 hours, then is cooled down to about 10° C., the formed product is filtered off and the filtration cake is washed on the filter with cold water.

By oven-drying the cake at 100° C., 77.9 g of product:

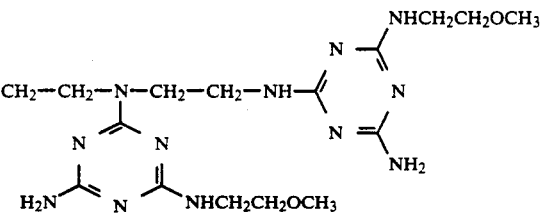

is obtained as a crystalline powder with m.p.=296°–299° C.

EXAMPLE 7

400 cm³ of water, 86.2 g of intermediate (X) and, with stirring, 20.6 g of diethylenetriamine are charged to the same apparatus of 1 liter of capacity as of preceding Example 6.

The reaction mass is heated up to 80° C. and is maintained at that temperature for 2 hours, then 16 g of sodium hydroxide dissolved in 30 cm³ of water is added.

The temperature of the reaction mixture is increased up to boiling point and the reaction mass is refluxed for 14 hours.

Then by operating in the same way as disclosed in preceding Example 6, 86.2 g of product:

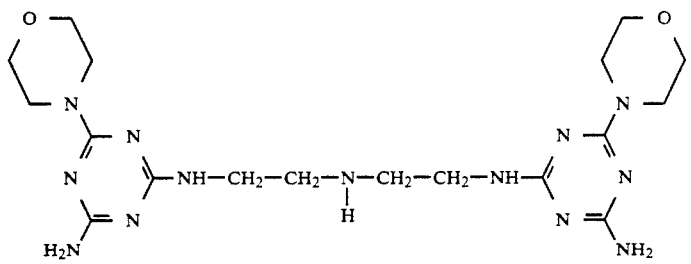
is obtained as a crystalline powder with m.p.=198°–201° C.
EXAMPLES 8–16
By operating under conditions analogous to those as disclosed in Examples from 1 to 7, the compounds of general formula (I) reported in Table 1 are synthesized, where Z is a triazinic ring of formula:
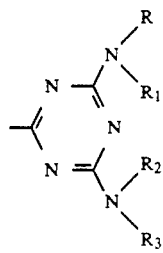

TABLE 1

| Example No. | R—N—R$_1$ | R$_2$—N—R$_3$ | $-N\begin{bmatrix}R_4\\(CH_2)_q-N\\\end{bmatrix}\begin{bmatrix}(CH_2)_s-N\\R_4\end{bmatrix}_t\begin{bmatrix}(CH_2)_q-N-\\R_4\end{bmatrix}_w$ | Melting point (°C.) |
|---|---|---|---|---|
| 8 | CH$_2$CH$_2$OCH$_3$ | morpholino | H | $-NH-(CH_2)_3-N-(CH_2)_3-NH-$ | 242–246 |
| 9 | piperidino | H | H | $-NH-CH_2CH_2-N-CH_2CH_2-NH-$ | 259–262 |
| 10 | morpholino | n-C$_4$H$_9$ | H | $-NH-CH_2CH_2-N-CH_2CH_2-NH-$ | 135–142 |
| 11 | CH$_2$CH$_2$CH$_2$N-morpholino | H | H | $N-(CH_2CH_2NH-)_3$ | 172–177 |
| 12 | CH$_2$OCH=CH$_2$ | morpholino | CH$_2$—CH=CH$_2$ | $-NH-(CH_2)_4-N-(CH_2)_3-NH-$ | 157–161 |
| 13 | (CH$_2$)$_5$OH | H | H | $-NH-(CH_2)_3-N-(CH_2)_2-N-(CH_2)_3-NH-$ | 199–204 |
| 14 | H | thiomorpholino | H | $-NH-CH_2CH_2-N-CH_2CH_2-NH-$ | 274–277 |
| 15 | H | H | t-C$_8$H$_{17}$ | $-NH-CH_2CH_2-N-CH_2CH_2-NH-$ | 122–127 |
| 16 | CH$_2$CH$_2$OCH$_3$ | CH$_2$CH$_2$OCH$_3$ | H | $-NH-CH_2CH_2-N-CH_2CH_2-NH-$ | 213–217 |

EXAMPLE 17

75.0 g of isotactic polypropylene flakes having a melt flow index of 12 and a content of 96% by weight of fraction insoluble in boiling n-heptane; 8.0 g of the product of Example 1; 16.0 g of ammonium polyphosphate (Exolit 422 by Hoechst); 0.67 g of dilaurylthiopropionate and 0.33 g of pentaerythritol tetra[3-(3,5-di-tert-butyl-4-hydroxyphenyl)propionate] are mix with one another and the resulting mixture is molded on a MOORE platen press, with a molding time of 7 minutes and a molding pressure of 40 kg/cm$^3$.

Specimens are obtained as small slabs of about 3 mm of thickness. On said specimens the level of self-extinguishment is determined by measuring the oxygen index (L.O.I. according to ASTM D-2863/77) on a STANTON REDCROFT apparatus, and applying the "vertical burning test" which makes it possible for the material to be classified at the three rating values 94 V-0, 94 V-1, and 94 V-2, according to UL 94 standards (published by Underwriters Laboratories, U.S.A.).

The following results are obtained:
L.O.I.=36.4
UL 94:Class V-0.

Although the invention has been described in conjunction with specific embodiments, it is evident that many alternatives and variations will be apparent to those skilled in the art in light of the foregoing description. Accordingly, the invention is intended to embrace all of the alternatives and variation that fall within the spirit and scope of the appended claims. The above mentioned references are hereby incorporated by reference.

We claim:

1. Triazinic compounds having the formula (I):

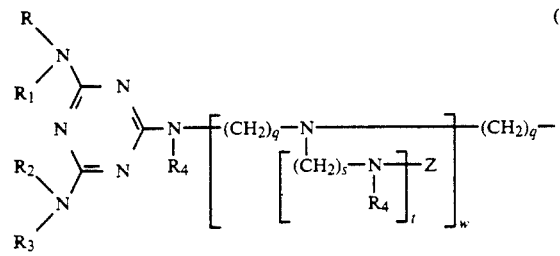

wherein:
t is either 0 or 1;
when t is equal to 0:
at least one of the radicals from R to R$_3$ is

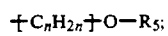

or

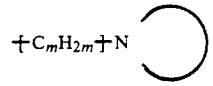

wherein:
n=an integer within the range of from 2 to 8;
m=an integer with the range of from 2 to 6;
R$_5$=H; (C$_1$-C$_8$)-alkyl; (C$_2$-C$_6$)-alkenyl; [C$_p$H$_{2p}$]O-R$_6$, wherein p is an integer within the range of from 1 to 4 and R$_6$ is either H or a (C$_1$-C$_4$)-alkyl; (C$_6$-C$_{12}$)-cycloalkyl or (C$_6$-C$_{12}$)-alkylcycloalkyl;
the group:

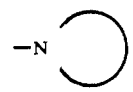

is replaced by a heterocyclic radical bonded to the alkyl chain through the nitrogen atom, wherein the heterocyclic radical is selected from the group consisting of aziridine; pyrrolidine; piperidine; morpholine; thiomorpholine; piperazine; 4-methylpiperazine and 4-ethylpiperazine; or in formula (I) at least one of the moieties:

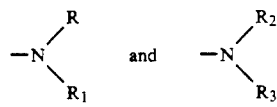

is replaced by a heterocyclic radical linked to the triazinic ring through the nitrogen atom wherein the heterocyclic radical is selected form the group consisting of aziridine; pyrrolidine; piperidine; morpholine; thiomorpholine; piperazine; 4-methylpiperazine; 4-ethylpiperazine; 2-methylpiperazine; 2,5-dimethylpiperazine; 2,3,5,6-tetramethylpiperazine; 2-ethylpiperazine and 2,5-dimethylpiperazine; the radicals R to R$_3$ are either equal to, or different from one another, and can have different meanings in each triazinic ring, have the abovesaid meaning, or they are: H; (C$_1$-C$_{18}$)-alkyl; (C$_2$-C$_6$)-alkenyl; (C$_6$-C$_{16}$)-cycloalkyl or (C$_6$-C$_{16}$)-alkylcycloalkyl, optionally substituted with a hydroxy or (C$_1$-C$_4$)-hydroxyalkyl function;
when t is equal to 1:
the radicals from R to R$_3$, which are either equal to, or different from one another, and can have different meanings in each triazinic ring, are: H; (C$_1$-C$_{18}$)-alkyl; (C$_2$-C$_6$)-alkenyl; (C$_6$-C$_{16}$)-cycloalkyl or (C$_6$-C$_{16}$)-alkylcycloalkyl, optionally substituted with a hydroxy or (C$_1$-C$_4$)-hydroxyalkyl function;

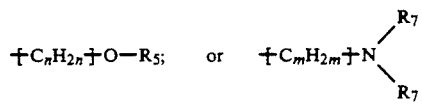

wherein:
n=an integer within the range of from 2 to 8;
m=an integer within the range of form 2 to 6;
R$_5$=H; (C$_1$-C$_8$)-alkyl; (C$_2$-C$_6$)-alkenyl; $+$C$_p$H$_{2p}+$O-R$_6$, wherein P is an integer within the range of from 1 to 4 and R$_6$ is either H or a ($C_1$–$C_4$)-alkyl; ($C_6$–$C_{12}$)-cycloalkyl or ($C_6$–$C_{12}$)-alkylcycloalkl; the radicals $R_7$, which can be either equal to, or different from one another are: H; ($C_1$–$C_8$)-alkyl; ($C_2$–$C_6$)-alkenyl;($C_6$–$C_{12}$)-cycloalkyl or ($C_6$–$C_{12}$)-alkylcycloalkyl; ($C_1$–$C_4$)-hydroxyalky; or the moiety:

is replaced by a heterocyclic radical linked to the alkyl chain through the nitrogen atom, wherein the heterocyclic radical is selected from the group consisting of aziridine; pyrrolidine; piperidine; morpholine; thiomorpholine; piperazine; 4-methylpiperazine and 4-ethylpiperazine; or in formula (I) at least one of the moieties:

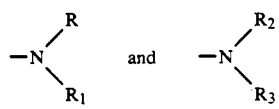

is replaced by a heterocyclic radical linked to the triazinic ring through the nitrogen atom wherein the heterocyclic radical is selected from the group consisting of aziridine; pyrrolidine; piperidine; morpholine; thiomorpholine; piperazine; 4-methylpiperazine; 4-ethylpiperazine; 2-methylpiperazine; 2,5 dimethylpiperazine 2,3,5,6-tetramethylpiperazine; 2-ethylpiperazine and 2,5-diethylpiperazine; $R_4$ is either hydrogen or ($C_1$–$C_4$)-alkyl; the indexes q, which can be either equal to, or different from each other, are integers within the range of from 2 to 5; s is and integer within the range of from 2 to 4; w is an integer within the range of from 1 to 5; z is hydrogen or:

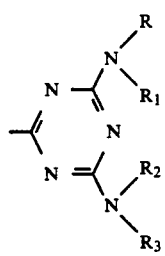

and its meaning can vary inside each repeating unit.

2. Process for preparing the triazinic compounds of formula (I) according to claim 1, wherein such compounds are obtained by the reaction of one mole of a polyamine having the formula (VI):

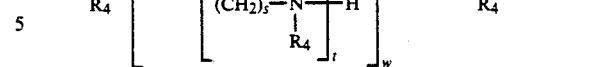

wherein $R_4$, q, s, t, and w have the same meaning as defined in claim 1, with a number of moles equal to, or smaller than, (2+w) of the intermediate (V):

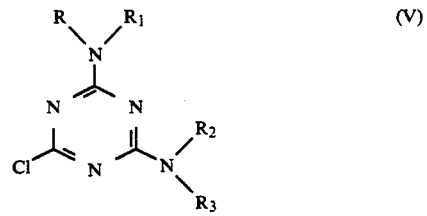

wherein the radicals from R to $R_3$ have the same meaning as defined in claim 1.

3. Process for preparing the triazinic compounds of formula (I) according to claim 1 wherein such compounds are obtained by the reaction of the intermediate of formula (VII):

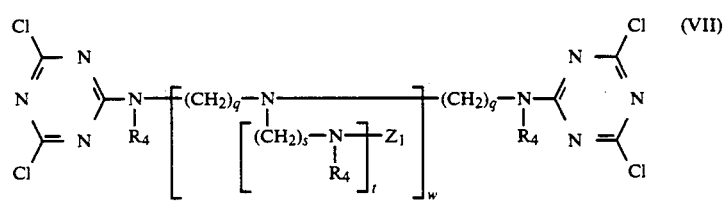

wherein $R_4$, q, s, t, and w have the same meaning as defined in claim 1 and $Z_1$ is hydrogen or:

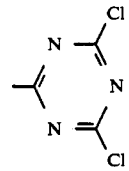

and its meaning can vary inside each repeating unit:
(a) with a number of moles lower than, or equal to, (2+w) of an amine of formula (II):

and then of an amine of formula (IV):

wherein the radicals from R to $R_3$ have the same meaning as defined in claim 1; or:
(b) with a number of moles lower than, or equal to, 2(2+w) of an amine of formula (II).

* * * * *